(12) United States Patent
Dzekunov et al.

(10) Patent No.: US 7,991,559 B2
(45) Date of Patent: Aug. 2, 2011

(54) COMPUTERIZED ELECTROPORATION

(75) Inventors: Sergey M. Dzekunov, Germantown, MD (US); Sarah H. Wang, Naperville, IL (US); Arthur D. Hanson, Harpers Ferry, WV (US)

(73) Assignee: Maxcyte Inc., Gaithersburg, MD (US)

( * ) Notice: Subject to any disclaimer, the term of this patent is extended or adjusted under 35 U.S.C. 154(b) by 976 days.

(21) Appl. No.: 11/291,118

(22) Filed: Nov. 30, 2005

(65) Prior Publication Data

US 2006/0172422 A1    Aug. 3, 2006

Related U.S. Application Data

(60) Provisional application No. 60/631,751, filed on Nov. 30, 2004.

(51) Int. Cl.
*G01N 33/48* (2006.01)

(52) U.S. Cl. .......................................................... 702/19

(58) Field of Classification Search ................... 702/19
See application file for complete search history.

(56) References Cited

U.S. PATENT DOCUMENTS

| | | | |
|---|---|---|---|
| 5,612,207 A | 3/1997 | Nicolau et al. ............. 435/173.6 |
| 5,720,921 A | 2/1998 | Meserol ........................ 422/44 |
| 6,074,605 A | 6/2000 | Meserol et al. ................ 422/33 |
| 6,090,617 A | 7/2000 | Meserol ..................... 435/285.2 |
| 6,485,961 B1 | 11/2002 | Meserol ..................... 435/285.2 |
| 6,617,154 B1 | 9/2003 | Meserol ..................... 435/285.2 |
| 6,773,669 B1 | 8/2004 | Holaday et al. ................. 422/44 |
| 7,328,064 B2 * | 2/2008 | Mathiesen et al. .............. 604/21 |
| 2003/0129716 A1 | 7/2003 | Ragsdale et al. ........... 435/173.6 |
| 2003/0144711 A1 * | 7/2003 | Pless et al. ....................... 607/60 |
| 2006/0199196 A1 * | 9/2006 | O'Banion et al. ................ 435/6 |

OTHER PUBLICATIONS

U.S. Appl. No. 10/225,446, filed Aug. 21, 2002, Dzekunov et al.
U.S. Appl. No. 11/127,557, filed May 12, 2005, Dzekunov et al.
Huang et al., "Micro-Electroporation: Improving Efficiency and Understanding of Electrical Permeabilization of Cells," *Biomedical Microdevices*, 2:145-150, 1999.

* cited by examiner

*Primary Examiner* — Jerry Lin
(74) *Attorney, Agent, or Firm* — Fulbright & Jaworski L.L.P.

(57) ABSTRACT

Techniques for computerized electroporation. An electroporation apparatus may be controlled according to one of a plurality of previously-saved, user-defined processing protocols. A processing log associated with a processing protocol may be generated, and the processing log may include patient or sample specific information. The processing log or a summary of the processing log may be exported to a user. Interactive instructions may be provided to a user. Those instructions may correspond to one or more steps of a processing protocol.

21 Claims, 7 Drawing Sheets

MaxCyte GT Experiment

Experiment ID : Baylor CLL-B 040510 1118
Experiment Date : 5/10/04 11:18:22 AM
Instrument ID : 003RG
Use # : 94

Protocol Title : Baylor CLL-B
Protocol ID : C2046E4B-ED11-E336-A837-C39E13D2C017
Processing Chamber : CL-1

Patient ID 1 : P1376
Patient ID 2 : C-2126.12
Patient ID 3 :
Processing Chamber Lot # : 85400
Processing Chamber Serial # : 913

Process Status : Process Successful.

Notes : CLIPA protocol. CD40L electrotransfection

File created : 11/1/04

FIG. 8

Date : 5/10/04 11:18:22 AM

Instrument ID : 003RG
Use Number : 94
Protocol Title : Baylor CLL-B
Protocol ID : C2046E4B-ED11-E336-A837-C39E13D2C017
Protocol Description : Protocol for CLIPA
Protocol Notes :
Protocol Uses : 10
Protocol Created : 4/13/04 3:26:17 PM
Protocol Last Modified : 5/10/04 10:09:06 AM Processing Chamber : 8

Access Level : Customer

Voltage : 640
PW1 : 200
PW2 : 0
Pulses in Burst : 1
Time Between Pulses : 150
Time between Bursts : 1000
Number of Bursts : 4
Burst Type : Monophasic
First Pulse Polarity : Negative
Set Temperature : 30

Processing Chamber : CL-1
Patient ID 1 : P1376
Patient ID 2 : C-2126.12
Patient ID 3 :
Processing Chamber Lot# : 85400
Processing Chamber Serial# : 913
Notes : CLIPA protocol. CD40L electrotransfection Bursts Delivered : 4
Cycles Delivered : 0
Cycles Requested : 0
Elapsed Time : 4.016s
Process Status : Process Successful.

Sample Number,Volts,Current

FIG. 9

COMPUTERIZED ELECTROPORATION

This application claims priority to, and incorporates by reference, U.S. Provisional Patent Application Ser. No. 60/631,751, which was filed on Nov. 30, 2004.

BACKGROUND OF THE INVENTION

1. Field of the Invention

The present invention relates generally to electroporation and flow electroporation. More particularly, it concerns software and other computer-related aspects of electroporation.

2. Description of Related Art

The process of electroporation generally involves the formation of pores in cell membranes, or in any vesicles, by the application of an electric field. During a poration process, cells may be suspended in a liquid media and then subjected to an electric field pulse. The medium may be electrolyte, non-electrolyte, or a mixture of electrolytes and non-electrolytes. The strength of the electric field applied to the suspension and the length of the pulse (the time that the electric field is applied to a cell suspension) typically varies according to the cell type.

Many electroporation methods disclosed in the art are not suitable for processing large volumes of sample, nor use of a high or repetitive electric charge. Furthermore, the methods are not suitable for use in a flow electroporation chamber. Many electroporation chambers are designed for static use only.

Regardless of the type of electroporation equipment being considered—flow or otherwise—the art does not make available advanced computerized techniques for controlling electroporation equipment and different electroporation processes. Control of equipment such as pumps, electrodes and signal generators, valves, and data analysis has typically been done completely, or mostly, manually through a traditional trial and error processes. Any particular electroporation process typically requires one or more trained technicians to manually adjust or set several parameters of several different pieces of equipment according to specialized (and sometimes exclusive) knowledge gained mostly through past trial and error. Effective and meaningful integration of patient data into electroporation protocols and routines has been lacking.

Although relying on traditional techniques may provide suitable results, they are not ideal and leave room for improvement. For example, traditional techniques can be significantly improved by providing techniques that allow one to, e.g., implement several different electroporation protocols that can be run efficiently, repeatedly, and accurately by technicians with little or no specialized knowledge about the details of underlying electroporation equipment. Making more effective use of patient data in electroporation protocols and routines would also represent a significant improvement.

Referenced shortcomings of conventional methodologies mentioned above are not intended to be exhaustive, but rather are among several that tend to impair the effectiveness of previously known techniques concerning electroporation. Other noteworthy problems may also exist; however, those mentioned here are sufficient to demonstrate that methodology appearing in the art has not been altogether satisfactory and that a significant need exists for the techniques described and claimed here.

SUMMARY OF THE INVENTION

Certain shortcomings of the prior art are reduced or eliminated by techniques disclosed here. These techniques are applicable to a vast number of applications, including but not limited to any application involving electroporation. These techniques may be implemented in hardware (e.g., a system including at least an electroporation apparatus and suitably-configured computer), software (implemented on any of a host of media known in the art), as a method, or as otherwise understood by those having ordinary skill in the art. The summary below is focused on inventive techniques implemented in a system or method, with the understanding that other analogous implementations are contemplated, such as software.

In one respect, the invention involves a system including an electroporation apparatus and a particularly-configured computer. The electroporation apparatus is configured to subject a sample to electrical energy sufficient to effect electroporation. The computer is coupled to the electroporation apparatus and is configured to control the electroporation apparatus according to one of a plurality of previously-saved, user-defined processing protocols.

In other respects, the computer may be further configured to generate a processing log associated with a processing protocol, the processing log including patient information. The computer may be further configured to export the processing log or a summary of the processing log to a user. The processing log or summary may be exported as text, a word processing file, a portable document format file, an e-mail, or a facsimile. The processing log or summary may be exported in an encrypted format. The processing log may include a plurality of fields selected from the group consisting of: file, data, instrument identification, use number, protocol title, protocol description, protocol uses, protocol created, protocol last modified, processing chamber, access level, electrical information, electroporation equipment information, sample specific information, and patient information. The computer may be further configured to control access to the processing log according to a security level.

In still other respects, the computer may be further configured to provide interactive instructions to a user, the instructions corresponding to one or more steps of a processing protocol. The interactive instructions may include instructions for checking hardware status of the electroporation apparatus. The interactive instructions may include instructions for assembling or activating one or more components of the electroporation apparatus. The interactive instructions may include instructions for handling a sample for introduction into the electroporation apparatus. The interactive instructions may include instructions for the user to input a data field. The data field may include a lot or serial number corresponding to a sample. A previously-saved, user-defined processing protocol may correspond to a processing protocol of a previous experiment.

In another respect, the invention involves a system including an electroporation apparatus and a particularly-configured computer. The electroporation apparatus is configured to subject a sample to electrical energy sufficient to effect electroporation. The computer is coupled to the electroporation apparatus and is configured to automatically correlate information assigned to the sample with a processing protocol and execute the protocol to electroporate the sample.

In other respects, the processing protocol may include a previously-saved, user-defined processing protocol. The information may include patient information. The patient information may include a patient identification or a patient condition. The information may include information in a form configured for electronic scanning. The form may include a bar code. The information may include a protocol designation corresponding to a previously-saved processing protocol. The information may include a protocol designation corresponding to a new processing protocol.

In another respect, the system involves a system including an electroporation apparatus and a particularly-configured computer. The electroporation apparatus is configured to subject a sample to electrical energy sufficient to effect electroporation. The computer is coupled to the electroporation apparatus and is configured to: (i) scan the sample to identify information assigned to the sample; (ii) input the information; (iii) correlate the information with a pre-existing, processing protocol; and (iv) execute the protocol to electroporate the sample.

In another respect, the invention involves a method in which an electroporation apparatus is controlled with a computer according to one of a plurality of previously-saved, user-defined processing protocols. A sample is subjected a to electrical energy sufficient to effect electroporation according to the previously-saved, user-defined processing protocol. The electroporation apparatus may be a flow electroporation apparatus, and the sample may be subjected to the electrical energy while the sample is flowing within the flow electroporation apparatus. The method may also include generating a processing log associated with a processing protocol, the processing log including patient or sample specific information. The method may also include exporting the processing log or a summary of the processing log in an encrypted format. The processing log may include a plurality of fields selected from the group consisting of: file, data, instrument identification, use number, protocol title, protocol description, protocol uses, protocol created, protocol last modified, processing chamber, access level, electrical information, electroporation equipment information, sample specific information, and patient information. The method may also include controlling access to the processing log according to a security level. The method may also include controlling access to the electroporation apparatus according to a security level and generating an audit trail that stores one or more activities of an authorized user. The method may also include providing interactive instructions to a user, the instructions corresponding to one or more steps of a processing protocol. The interactive instructions may include instructions for (i) checking hardware status of the flow electroporation apparatus or (ii) assembling or activating one or more components of the flow electroporation apparatus. The previously-saved, user-defined processing protocol may correspond to a processing protocol of a previous experiment. The method may also include determining if one or materials are validated for use with the electroporation apparatus and prohibiting use if one or more materials are not validated.

In another respect, the invention involves a method in which information assigned to a sample is automatically correlated with an electroporation processing protocol. The protocol is executed to electroporate the sample. The processing protocol may include a previously-saved, user-defined processing protocol. The information may include patient or sample specific information. The information may include information in a form configured for electronic scanning. The form may include a bar code. The information may include a protocol designation corresponding to a previously-saved processing protocol. The information may include a protocol designation corresponding to a new processing protocol.

In another respect, the invention involves a method in which a sample is scanned to identify information assigned to the sample. The information is input. The information is correlated with a pre-existing, electroporation processing protocol, and the protocol is executed to electroporate the sample. The scanning may include use of a radio frequency identification (RFID) tag and reader.

In another respect, the invention involves a computer readable media including computer-executable instructions for executing the methods described above and herein.

As used herein, "flow" electroporation refers to electroporation associated with a sample that flows continuously or intermittently (e.g., intermittently in cycles or recurrently) by electrodes of an electroporation chamber within an electroporation system that handles flowing samples. "Flow" electroporation is therefore distinguished from traditional, static electroporation systems that process samples statically, batch by batch, within a system that does not handle flowing samples. Different electroporation and "flow" electroporation techniques are discussed in, for example, U.S. patent application Ser. No. 11/127,557; U.S. patent application Ser. No. 10/225,446; U.S. Pat. No. 5,612,207; U.S. Pat. No. 5,720,921; U.S. Pat. No. 6,074,605; U.S. Pat. No. 6,090,617; U.S. Pat. No. 6,485,961; U.S. Pat. No. 6,617,154; and/or U.S. Pat. No. 6,773,669 (each of which is incorporated here by reference). Likewise a "flowing" sample refers to continuous or intermittent (e.g., intermittently in cycles or recurrently) flow of a sample.

As used herein, an electroporation "apparatus" or flow electroporation "apparatus" refers to any equipment used directly or indirectly to effect the electroporation. An electroporation "apparatus" or flow electroporation "apparatus" therefore encompasses one or more electroporation chambers, pumps, valves, reservoirs, inlets, outlets, and/or associated elements. An electroporation "apparatus" or flow electroporation "apparatus" also encompasses electronics and computer equipment used directly or indirectly for the electroporation process such as detectors, electrical signal generators, temperature sensors, pressure sensors, flow sensors, volume sensors, chemical sensors, heating elements, and/or cooling elements.

In preferred embodiments, the techniques of this disclosure are adapted for use with flow electroporation and with flow electroporation apparatuses. However, the techniques are equally applicable to any type of electroporation, and so embodiments are described generally with respect to electroporation. Those having ordinary skill in the art will comprehend that application to electroporation or flow electroporation is one of choice.

As used herein, a "processing protocol" refers to a set of rules describing how to process a sample for electroporation. The rules may be embodied as a set of computer-readable instructions or parameters. For example, a script file or configuration file may be used to embody a protocol. An example script or configuration file may include instructions corresponding to equipment settings (e.g., one set of instructions may involve voltage settings while other instructions may speak to electrical pulse timing).

As used herein, a "processing log" refers to recorded information regarding or resulting from one or more electroporation sessions. A processing log "associated with" a processing protocol simply means that a log includes data that comes about due to the execution of a particular processing protocol. In a representative embodiment, a processing log includes electroporation equipment information, processing protocol information, electroporation electrical parameters, and/or patient information.

As used herein, "control" or "controlling" with respect to an electroporation apparatus means affirmative activation or regulation of one or more components of the apparatus so as to affirmatively control an electroporation process. Control is preferably in concert when a plurality of components are involved. The control of the electroporation apparatus is, in preferred embodiments tailored specifically so that electroporation is effected, and more particularly so that it is effected according to a processing protocol such as a previously-saved, user-defined processing protocol. For example, the protocol may dictate the shape, pattern, voltage, current, polarity, timing, duration, interval etc. (alone or in combination) of electrical pulses. The protocol may dictate the activation or regulation of, e.g., valves or manifolds. The protocol may dictate the activation or regulation of, e.g., detectors, electrical signal generators, temperature sensors, pressure sensors, flow sensors, volume sensors, chemical sensors, heating elements, and/or cooling elements. The activation or regulation of all of these, or other components, may be done individually or in concert in any combination. For example, pulsing conditions may be controlled in concert with valve conditions, which may be controlled in concert with sensors, etc.

Other features and associated advantages will become apparent with reference to the following detailed description of specific, example embodiments in connection with the accompanying drawings.

BRIEF DESCRIPTION OF THE DRAWINGS

The following drawings form part of the present specification and are included to further demonstrate certain aspects of the invention. The invention may be better understood by reference to one or more of these drawings in combination with the detailed description of example embodiments presented here. The drawings are examples only. They do not limit the claims.

FIGS. 8-9 are example process log outputs, in accordance with embodiments of this disclosure.

DESCRIPTION OF ILLUSTRATIVE EMBODIMENTS

The computerized electroporation techniques of this disclosure can be applied to any electroporation system to allow several different electroporation protocols to be run efficiently, repeatedly, and accurately by technicians with little or no specialized knowledge about the details of underlying electroporation equipment. The techniques also make more effective use of patient data or sample specific information in electroporation protocols. Patient data can be important when the electroporation, flow or otherwise, is being used to study and/or treat a sample from a patient. As stated previously, the techniques can be applied for flow electroporation or other types of electroporation. Techniques concerning patients can be applied to human patients or any other biological subject. Techniques of this disclosure may allow for compliance with regulatory requirements in a manufacturing environment including, for example, appropriate line clearance and change control procedures, manufacturing process controls, maintenance of chain of identity and chain of custody, forward and backward traceability of samples, reagent, processing assemblies and audit trail for electroporation process related data.

Figure 1:
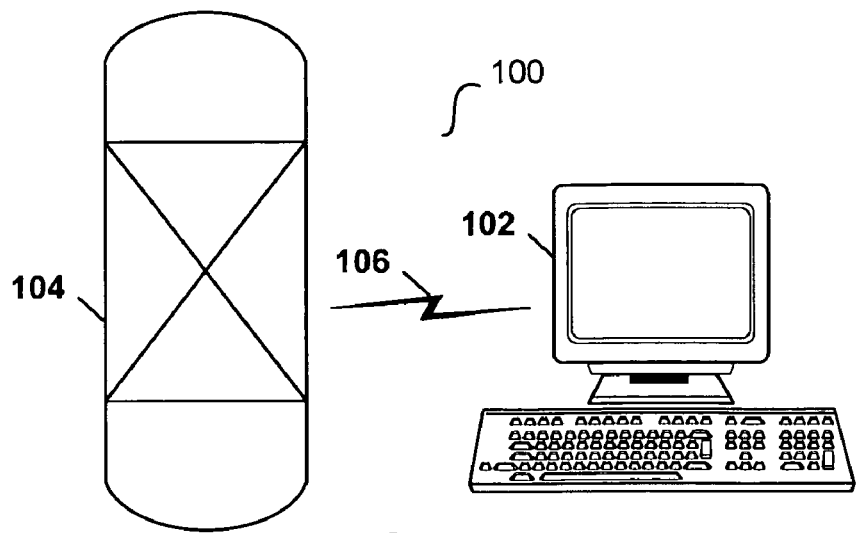
FIG. 1 is a schematic diagram of an electroporation system, in accordance with embodiments of this disclosure. In a preferred embodiment, the system of FIG. 1 is a flow electroporation system.

FIG. 1 is a schematic diagram of an electroporation system 100, in accordance with embodiments of this disclosure. FIG. 1 shows an electroporation apparatus 104 coupled to computer 102 via connection 106. Electroporation apparatus 104 may be, in one embodiment, a flow electroporation apparatus. In other embodiments, it may be a non-flow device.

Electroporation apparatus 104 is meant to indicate any electroporation apparatus to which the computerized techniques of this disclosure may be applied. Electroporation apparatus 104 may include any electroporation equipment or flow electroporation equipment, such as but not limited to that described in at least U.S. patent application Ser. No. 11/127,557; U.S. patent application Ser. No. 10/225,446; U.S. Pat. No. 5,612,207; U.S. Pat. No. 5,720,921; U.S. Pat. No. 6,074,605; U.S. Pat. No. 6,090,617; U.S. Pat. No. 6,485,961; U.S. Pat. No. 6,617,154; and/or U.S. Pat. No. 6,773,669 (each of which has been incorporated by reference). Electroporation apparatus 104 may also encompass any other electroporation apparatus known or available in the art. Those having ordinary skill in the art will appreciate that such electroporation apparatuses may be modified and/or or optimized and still be suitable for implementing the techniques of this disclosure.

For example, in one embodiment, electroporation apparatus 104 may use electrodes made from materials including metals and/or non-metallic conductors. For example, in some embodiments, gold, platinum, tantalum, or carbon (graphite, diamond) may be used.

Connection 106 is meant to indicate any connection suitable for allowing computer 102 to communicate with electroporation apparatus 104. In one embodiment, connection 106 is a wired connection. In another embodiment, connection 106 is wireless. In a wireless embodiment, connection 106 may be a network connection over a network such as the Internet. Such an embodiment allows for remote control of electroporation apparatus 104 from virtually any computer in the world connected to the Internet. In one embodiment, computer 102 and electroporation apparatus 104 are integral. In such an embodiment, connection 106 may be an internal connection.

Computer 102 is meant to indicate any computing device capable of executing instructions for controlling one or more aspects of electroporation apparatus 104. In one embodiment, computer 102 is a personal computer (e.g., a typical desktop or laptop computer operated by a user of the electroporation apparatus 104). Such a computer may include one or more appropriate boards for interfacing with electroporation apparatus 104. In another embodiment, computer 102 may be a personal digital assistant (PDA) or other handheld computing device. In another embodiment, computer 102 and electroporation apparatus 104 may be integral, and in such embodiment, computer 102 may simply constitute one or more boards (e.g., a motherboard including a processor) among other electronic boards and equipment.

Computer 102 can be a networked device and may constitute a terminal running software from a remote server, wired or wirelessly. Input from a user may be gathered through one or more known techniques such as a keyboard and/or mouse. Output, if necessary, can be achieved through one or more known techniques such as an output file, printer, facsimile, e-mail, web-posting, or the like. Storage can be achieved internally and/or externally and may include, for example, a hard drive, CD drive, DVD drive, tape drive, floppy drive, network drive, flash, or the like. Computer 102 may use any type of monitor or screen known in the art. For example, a cathode ray tube (CRT) or liquid crystal display (LCD) can be used. One or more display panels may also constitute a display. In other embodiments, a traditional display may not be required, and computer 102 may operate through appropriate voice and/or button commands.

Security associated with computer 102 can involve any techniques known in the art. Computer 102 may be associated with one or more biometric readers that only allow authorized personnel to operate the equipment. In other embodiments, user accounts and passwords may be used. In yet other embodiments, security functionality may be disabled or not present.

Figure 2:
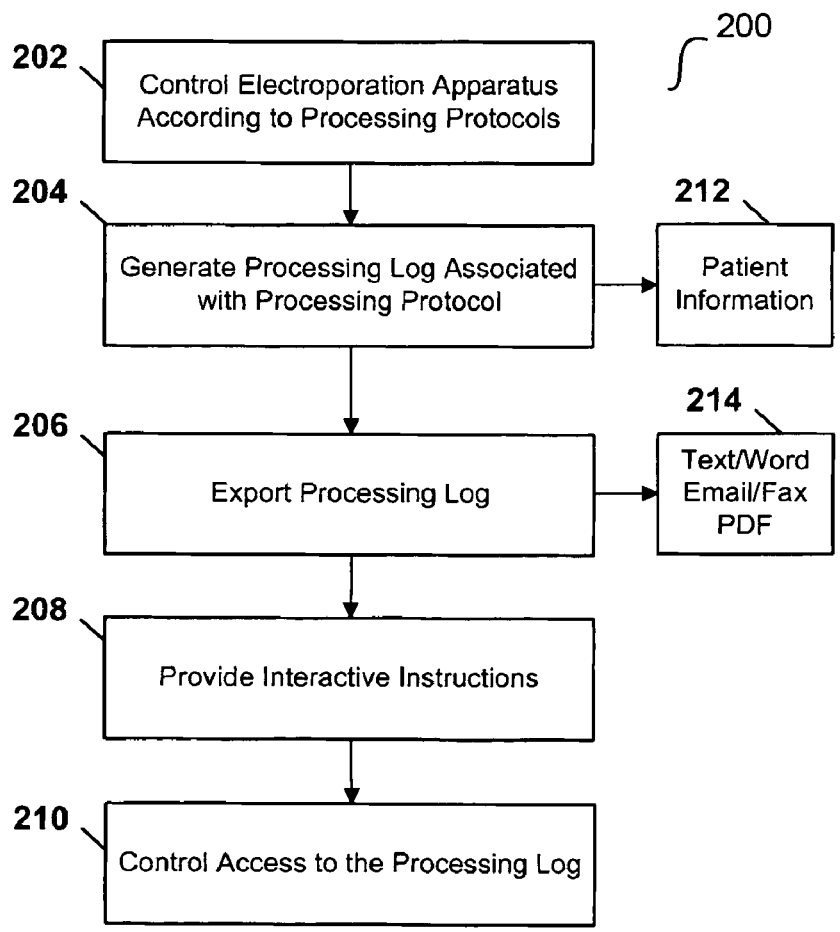
FIG. 2 is a flow chart showing steps of a computerized electroporation method, in accordance with embodiments of this disclosure. In a preferred embodiment, the computerized electroporation method of FIG. 2 is applied for flow electroporation.

FIG. 2 is a flow chart showing steps of a computerized electroporation method 200, in accordance with embodiments of this disclosure. Computer 102 of FIG. 1 is configured to implement the steps of FIG. 2. In general, an embodiment of method 200 allows a user, among other things, to operate an electroporation apparatus 104 easily, repeatedly, and efficiently using intuitive, previously-saved, user-defined processing protocols. For example, instead of programming a run sequence for each sample based on specialized knowledge, a technician may simply process a sample according to a pre-saved processing protocol that has all the expertise of a trained specialist already "built-in." This allows electroporation processes to be run by those with little or no experience.

In step 202, computer 102 controls electroporation apparatus 104 according to one or more processing protocols. In one embodiment, a set of rules constituting a processing protocol is accessed by computer 102. The set of rules can be embodied in any computer readable format known in the art. In one embodiment, the rules make up a script or configuration file. The rules are followed by computer 102 to control one or more aspects of electroporation. For example, the rules are followed to do tasks such as, but not limited to:
- drive electrodes according to particular electrical and timing parameters;
- drive one or more pumps to transport sample;
- drive one or more pumps to transport washing solution or other material;
- open and close valves;
- diagnostics (pre- and post-operations check);
- data analysis;
- access one or more sensors; and/or
- react to readings of one or more sensors by producing digital or analog output that may drive an electroporation or an associated process (e.g., cooling, heating, mixing, aeration, analysis of sensor data, triggering an alarm, and sampling handling).

In one embodiment, processing protocols are user-defined. A user can therefore dictate one or more settings of a protocol. For example, assuming a processing protocol is embodied in a script or configuration file, that script or configuration file may be edited by a user to change settings (e.g., electroporation rules) according to need. In one embodiment, a processing protocol can be edited or modified in an intuitive manner using a graphical user interface (GUI). For example, a user may use a mouse to select a parameter and enter a desired value or setting. Pull down menus, text or numeric fields, button toggles, or any other data entry/revision techniques known in the art may be used to this end. For example, a user may use a mouse to select a "pulsing options" field and use a pull-down menu to select pulsing parameters suitable for a particular experiment. For example, a user may dictate pulse shape, pattern, voltage, current, polarity, timing, duration, interval, etc.

In one embodiment, processing protocols may be saved. Protocols may be named and used for future use. When a new protocol is created, it may be saved automatically. Automatic saves may follow a defined naming mechanism. For example, protocols may be given a filename corresponding to the creation date of the protocol. Another possible naming protocol, among many, may assign filenames with a numeral that advances sequentially—the first saved protocol may be, e.g., Prot_00001.txt while the second protocol may be Prot_00002.txt, etc. In one embodiment, a user may choose to implement a processing protocol of a previous experiment, or simply modify one or more settings of a previous experiment. Such functionality may be particularly useful if a user finds himself or herself only changing a few (or zero) parameters from one electroporation run to the next.

In one embodiment, processing protocols may be installed from a remote location. For example, a protocol may be generated "off-site" and submitted to a remote machine for eventual execution. Such an embodiment may provide significant advantages where, e.g., a researcher is located remotely from one or more electroporation machines that are carrying out experiments or treatment.

In step 204, a processing log is generated, which is associated with a processing protocol. In a representative embodiment, a processing log is generated upon completion of an electroporation session. However, in other embodiments, at least portions of the processing log may be generated beforehand (e.g., a processing log may include patient or sample specific information and other fields prior to completion of a session). Element 212 indicates that a processing log may contain patient information. A processing log may also contain, e.g., sample specific information. Example patient information may include, but is not limited to, one or more of a patient's name or other identifier, age, sex, weight, race, insurance information, condition being treated, number of times the patient has been treated, past treatments for the patient, type of sample drawn from the patient, etc. In one embodiment, a patient identifier may correspond to a guaranteed unique identification designation (e.g., identification number or alphanumeric string) for each patient. In one embodiment, a guaranteed unique identification designation may be associated with codes and one or more associated algorithms for generating N different unique values, with N being equal to, or greater than, the population of the earth. Patient information may be tailored to comply with one or more regulations existing in the art. For example, patient information may be kept, organized, displayed, or formatted according to the requirements of the Food and Drug Administration (FDA), and/or pertinent laws (e.g., confidentiality laws concerning patients or medical records).

Other example fields of a processing log include, but are not limited to, a file name, data, instrument identification, use number, protocol title, protocol description, protocol uses, protocol created, protocol last modified, processing chamber, access level, electroporation equipment information, and electrical information. The data may include any data from the electroporation apparatus 104. For example, pressure, temperature, electrical, contaminant, or other readings may be recorded. Instrument identification may identify a particular electroporation apparatus 104 by name or other identifier. Use number may indicate the number of times a particular electroporation apparatus 104 and/or processing protocol has been used. Protocol title may identify a particular processing protocol. A protocol description may summarize rules of a particular processing protocol. Protocol uses may count how many times a particular processing protocol has been used. Protocol created records the date on which a particular processing protocol was created (e.g., saved to a file). Protocol last modified may indicate when a particular processing protocol was most-recently changed (e.g., edited and then saved to file). Processing chamber may identify a particular chamber used within a particular electroporation apparatus 104. Access information may indicate a security level associated with a particular electroporation apparatus 104, a particular processing protocol, a particular process log, or a combination thereof. Finally, electrical information may pertain to electrical data associated with an electroporation session. For example, voltage and current information may be recorded. Pulse shape, pattern, polarity, timing, duration, interval, etc. may be recorded.

Step 206 indicates that a processing log may be exported. A processing log may be saved in any format known in the art. Likewise, it may be exported in any manner known in the art. Element 214 indicates that a processing log can be exported as text, a word processing file, an e-mail, a fax, or a portable document format (PDF) file. These are of course examples only. For instance, a processing log may be exported to a spreadsheet or another program capable of generating one or more graphs or charts. Alternatively, the processing log itself may automatically generate graphs, charts, reports, or other graphics to more effectively illustrate information. In general embodiments, a processing log may encompass any form of alphanumeric, visual (e.g., pictures, graphs, drawings), and/or coded content known in the art. Any output may be user-defined and customizable. For example, any or all aspects of the layout, style, and arrangement of information may be dictated by a user.

A processing log may be exported in full or in a summary form. An exported summary may be useful to users who simply want a snapshot of a particular process. A user may define which fields to include in a summary according to need or desire. The formatting of a summary may be dictated by a user. For example, fonts, font sizes, arrangement of information, color of information, types of charts, etc., may be user-defined and customizable to make the processing log summary more user-friendly.

For security reasons or otherwise, a processing log (full or summary) may be encrypted or otherwise protected against unauthorized access or reading. Encryption or other forms of protection may be implemented according to techniques well known in the art. Additional insight about security and access control is provided in the description below concerning step 210 of FIG. 2.

Step 208 indicates that computer 102 may provide a user with interactive instructions. Providing interactive instructions is particularly useful so that technicians with little or no experience with electroporation can be effectively guided through a particular processing protocol. Interactive instructions may also be useful to ensure that, e.g., important safety measures are followed each time an experiment is run.

In one embodiment, the interactive instructions correspond to one or more steps of a particular processing protocol. In one embodiment, the interactive instructions may entail instructions for checking hardware status of the electroporation apparatus 104. For example, a user may be reminded to check that a particular status light is a particular color or a particular meter is showing a reading within a particular range. In one embodiment, the interactive instructions may entail instructions for assembling or activating one or more components of the electroporation apparatus 104. For example, a user may be instructed how to load a sample or turn on the electroporation apparatus 104. Alternatively, a user may be instructed how to assemble or otherwise operate one or more pumps or valves. A user may be instructed how to troubleshoot equipment that is not operating properly, and such instructions may be automatically triggered if one or more sensor readings indicate that a problem is developing, or has developed. In one embodiment, the interactive instructions may entail instructions for handling a sample for introduction into the electroporation apparatus 104. For example, a user may be instructed how to insert a sample into the electroporation apparatus 104, how to remove a sample, or generally how to process a sample properly. Alternatively, a user may be instructed how to obtain a sample from a patient. In one embodiment, the interactive instructions may entail instructions for the user to input a data field such as, but not limited to, a lot or serial number corresponding to a particular sample.

Step 210 indicates that access to a processing log can be controlled by computer 102. For example, as mentioned above, encryption can be employed. In other embodiments, processing logs can be password protected, accessed only by those with particular biometric signature (e.g., fingerprint match), or any other access control method known in the art. This functionality may be particularly useful in protecting patient information, should it be included in a processing log. Access control to processing logs may be implemented according to state laws, national laws, and/or rules concerning medical patient's privacy.

Figure 3:
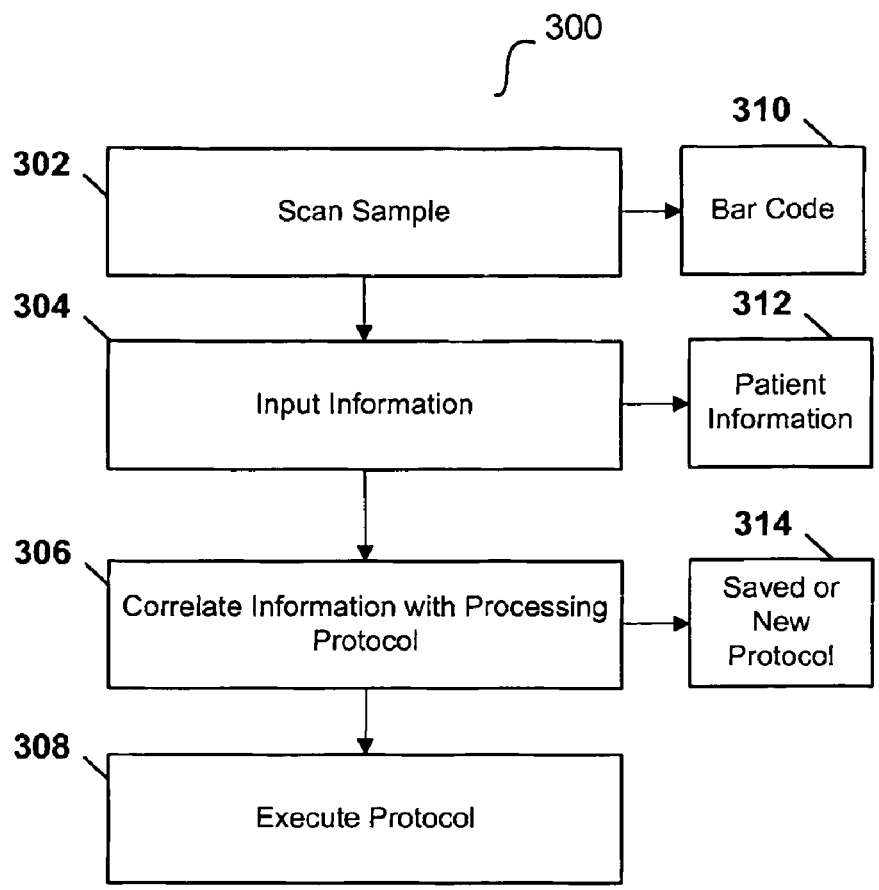
FIG. 3 is another flow chart showing steps of a computerized electroporation method, in accordance with embodiments of this disclosure. In a preferred embodiment, the computerized electroporation method of FIG. 3 is applied for flow electroporation.

FIG. 3 is another flow chart showing steps of a computerized electroporation method 300, in accordance with embodiments of this disclosure. In general, an embodiment of method 300 allows a user, among other things, to easily pick an appropriate processing protocol automatically or semi-automatically with low or reduced risk of improper processing. This functionality can be achieved by accessing and implementing a particular profile that correlates with information assigned to a particular sample. For example, a sample that should receive processing protocol "A" can be labeled with a bar code coding for protocol "A." Scanning that bar code accesses rules associated with processing protocol "A," which is then run by electroporation apparatus 104. User input error is reduced or eliminated. A user need not understand why a particular sample should receive a particular processing protocol, nor does he or she need to load a processing protocol manually.

In step 302, an electroporation sample is scanned. Scanning may be done by computer 102 or appropriate equipment in communication with computer 102. In one embodiment, step 302 may entail scanning a bar code associated with a sample, as indicated by element 310 of FIG. 3. In another embodiment, this step may entail use of a radio frequency identification (RFID) device associated with the sample, which is read by an appropriate reader in communication with computer 102.

In step 304, information from step 302 is input into computer 102. The inputting of information may be done automatically; a scan of a sample may identify information and automatically input it to computer 102. The information that is input may include patient information, as indicated by element 312. The information may also include, e.g., sample specific information. Patient information can include a patient identification or a patient condition. In another embodiment, the information may entail a protocol designation corresponding to a previously-saved processing protocol or a new processing protocol.

In step 306, information input in step 304 is correlated with a processing protocol. In one embodiment, a lookup table accessible by computer 102 may be used for the correlation procedure. For example, a bar code reading of "B" may have a lookup table entry correlating "B" with processing protocol "X." Therefore, any sample coded as "B" will receive electroporation settings and other parameters according to processing protocol "X." In one embodiment, processing protocol "X" may correspond to a particular treatment for patients coded "B" who each have the same or similar ailment. As indicated by element 314, the information input in step 304 may be correlated with a saved or a new processing protocol. Correlation with a saved processing protocol may be done with a lookup table or other known technique as described here.

Correlation with a new processing protocol may use the same or a varied technique. In one embodiment, input information may signal to computer 102 that a new processing protocol should be created. For instance, if a sample is coded as "NEW," computer 102 may be programmed to start a new processing protocol to accommodate that sample. Further information input in step 304 may dictate necessary settings or parameters to be applied to the new processing protocol. For example, if the sample is coded as "NEW-02 03 07," the "NEW" designation may signal computer 102 to generate a new processing protocol while the numbers that follow ("02 03 07") may inform computer 102 about what settings or parameters to populate that new processing protocol with. For instance, a first numeric or alphanumeric designator may signal pulsing parameters, a second numeric or alphanumeric designator may signal pump speed, a third numeric or alphanumeric designator may signal temperature settings, etc. Such designators can be coded into a bar code, a RFID device, or by any other means known in the art. In this manner, information assigned to a sample may be used to generate a customized processing protocol that had not been previously saved. Again, a technician therefore need not understand how to generate a new processing protocol and may process a sample even if that sample requires settings and parameters that are new.

In step 308, the processing protocol that correlates with the input information from steps 304 and 306 is executed. The electroporation apparatus 104 and computer 102 operate together to carry out the electroporation process called-for by the processing protocol.

Security, Auditing, Chain of Custody

As discussed above, various security mechanisms may be implemented in conjunction with the computerized electroporation techniques of this disclosure. In one embodiment, use of electroporation equipment may be restricted to registered users. Such users may be required to have passwords. For example, in order to use the electroporation apparatus, a password may need to be entered. In addition to or alternatively to passwords, one or more biometric identifiers may be used to increase security and may improve ease use for electroporation equipment since biometrics may eliminate the typing of identifiers. Again, these measures may act to restrict use to a pre-approved class and/or record their activities.

Software may implement restrictions on use. Such software may be configured to record the login and/or activities of each registered user. In other words, an audit trail may be created. In one embodiment, the stored audit trail may be encrypted or made tamper-resistant or tamper-proof. The user identity, procedures run, and time may be stored in one embodiment. Other embodiments may store additional or different information concerning the activities of a user. In one embodiment, every keystroke or activity of the user would be recorded and time-stamped.

In one embodiment, the audit trail may transmit data to a storage site. Such transmission may be automatic, and it may be to multiple sites. Changes to the data may be possible, but in one embodiment may be implemented only by pre-authorized personnel. The changes to the data may itself be stored in a different, or the same, audit trail.

In one embodiment, a "receipt" may be printed from electroporation equipment or a coupled device to show, e.g., what procedure or procedures were run, date of procedure, electroporation equipment settings, user identity, patient information, patient condition, sample specific information, or any other information managed or stored by an electroporation apparatus or an associated computer. This receipt may be signed by the user or other person to confirm the information printed thereon or to signify that the receipt is an official record. The receipt may form part of billing paperwork for a patient. The receipt may be submitted for reimbursement to a health care provider. The receipt may serve as yet another element in a chain of custody.

In different embodiments, it may be beneficial to ensure that only pre-approved protocols or materials are being used with electroporation equipment. In one embodiment, such validation may be done using bar-coded or RFID tagged material. A computer controlling the electroporation equipment may read the material and, prior to use of the electroporation equipment, ensure that the material is pre-approved for use with the electroporation equipment. Material that may be validated includes, but is not limited to, cells from patients, DNA to be loaded into the electroporation apparatus, buffer solutions or buffer lots, and electroporation chambers themselves. The computer may be programmed to only permit validated materials and/or compatible combinations of materials to be used for an electroporation run.

In one embodiment, a computer may access a "pick-list" of approved materials that act to ensure that only qualified or validated materials are used. A user may or may not be allowed to see this list. Bar code or RFID signatures may be listed in a lookup file or other storage mechanism so that they may be correlated with approved materials and updated periodically (automatically or manually). One or more users may be authorized to modify material lists, signature lists, lookup tables correlating entries, etc. Each material record or signature record stored within a file or otherwise may have a shorthand key to aid in retrieval or sorting of records. In one embodiment, certain materials' bar code(s) or RFID identification may be automatically removed from a list of approved materials at their expiration date. This helps prevent the use of non-validated materials or materials that are past their expiration. In one embodiment, these types of validation controls may be over-ridden by pre-authorized users. For example, a user having a high level of "clearance" may be able to use materials even if those materials are not pre-approved and not on a list.

Security and validation techniques discussed here may aid in the maintenance of chain of custody records. Since user's activities may be stored, one may reliably monitor what has happened to a particular sample or material. Additionally, since use of electroporation equipment may be limited to validated materials only, one may deduce further information about a particular experiment or electroporation run. Thus, these or similar techniques can provide for enhanced tracking of materials (both patient specific materials and manufactured ones), system operators, and processes carried out. The tracking can identify the time associated with each activity. Enhancement of the security of records is also improved using these techniques.

Figure 4:
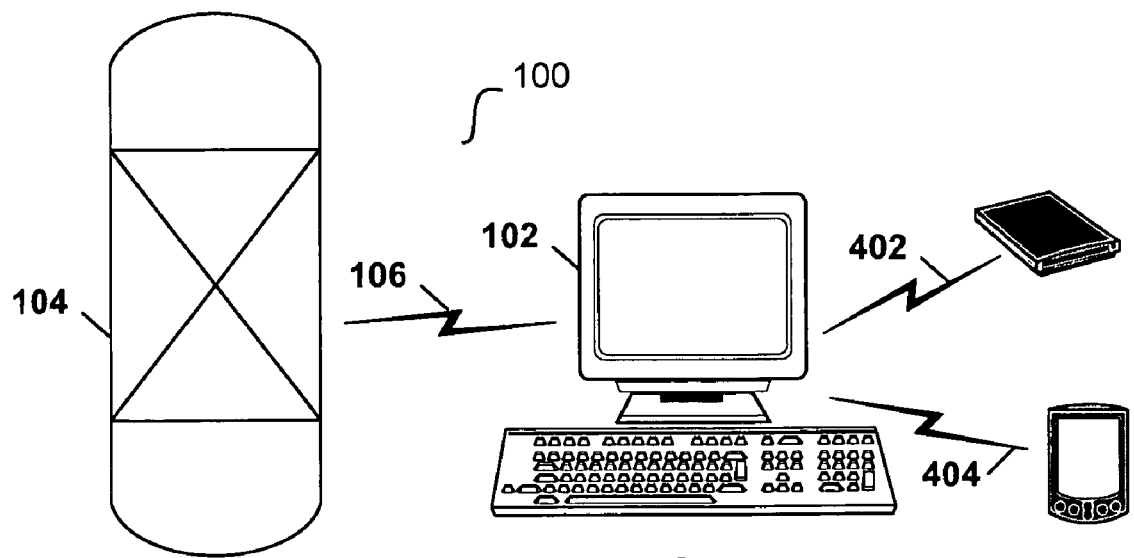
FIG. 4 is another schematic diagram of an electroporation system including external memory or associated devices, in accordance with embodiments of this disclosure. In a preferred embodiment, the system of FIG. 4 is a flow electroporation system.

FIG. 4 is another schematic diagram of an electroporation system including external memory or associated devices, in accordance with embodiments of this disclosure. In FIG. 4, the system 100 described in relation with FIG. 1 is shown, accompanied by storage device 402 and PDA 404. FIG. 4 is included simply to indicate that the techniques described here may be embodied in software or firmware residing in, or associated with a computing device such as computer 102 or PDA 404 (or any other computing device). The software can be embodied on any computer-readable media known in the art. For example, it may be embodied internally or externally on a hard drive, ASIC, CD drive, DVD drive, tape drive, floppy drive, network drive, flash, or the like. In this regard, storage device 402 may represent, e.g., an external CD drive or flash device. PDA 404 is included to show that the software can be housed in a handheld device or the like that can itself drive the techniques of this disclosure or can, alternatively, communicate with a different computer (such as computer 102) for implementation of electroporation processes.

The software for carrying out steps disclosed here can be written according to any technique known in the art. For instance, the software may be written in any one or more computer languages (e.g., ASSEMBLY, PASCAL, FORTRAN, BASIC, C, C++, C#, JAVA, etc.), adapted to provide instructions for carrying out the steps in, for instance, FIGS. 2 and 3.

In one embodiment, the software is part of a GUI, which may provide a technician a more intuitive feel when running the software. Different fields may be accessible by a mouse and/or keyboard. Alarms, cues, and the like may be done via pop-up windows, audible alerts, or any other techniques known in the art.

In one embodiment, portions of the software may be kept in-house, while other portions may reside with a customer.

The following examples are included to demonstrate specific embodiments of this disclosure. It should be appreciated by those of ordinary skill in the art that the techniques disclosed in the examples that follow represent techniques discovered by the inventors to function well in the practice of the invention, and thus can be considered to constitute specific modes for its practice. However, those of ordinary skill in the art should, in light of the present disclosure, appreciate that many changes can be made in the specific embodiments which are disclosed and still obtain a like or similar result without departing from the spirit and scope of the invention.

EXAMPLES

Figure 5:
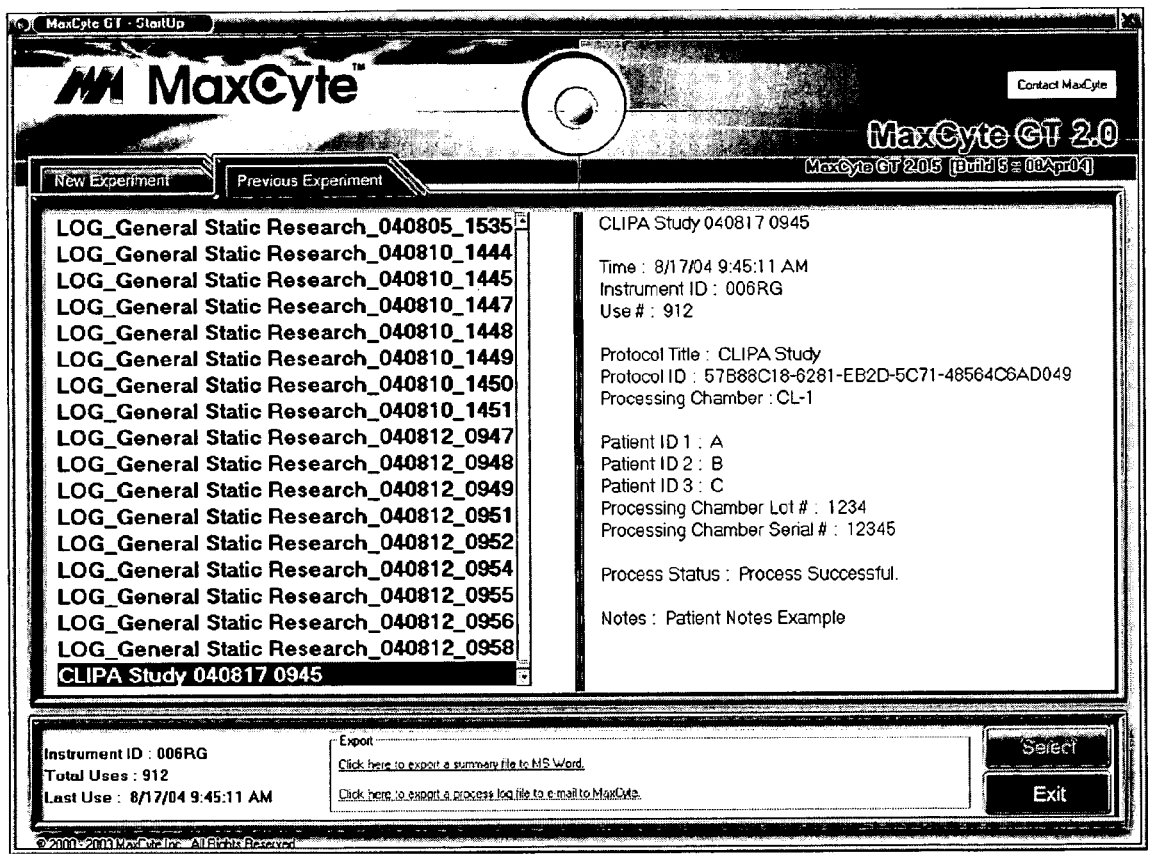
FIGS. 5-7 are example screen shots exhibiting computerized electroporation techniques, and particularly computerized electroporation techniques applied for flow electroporation, in accordance with embodiments of this disclosure.
Figure 6:
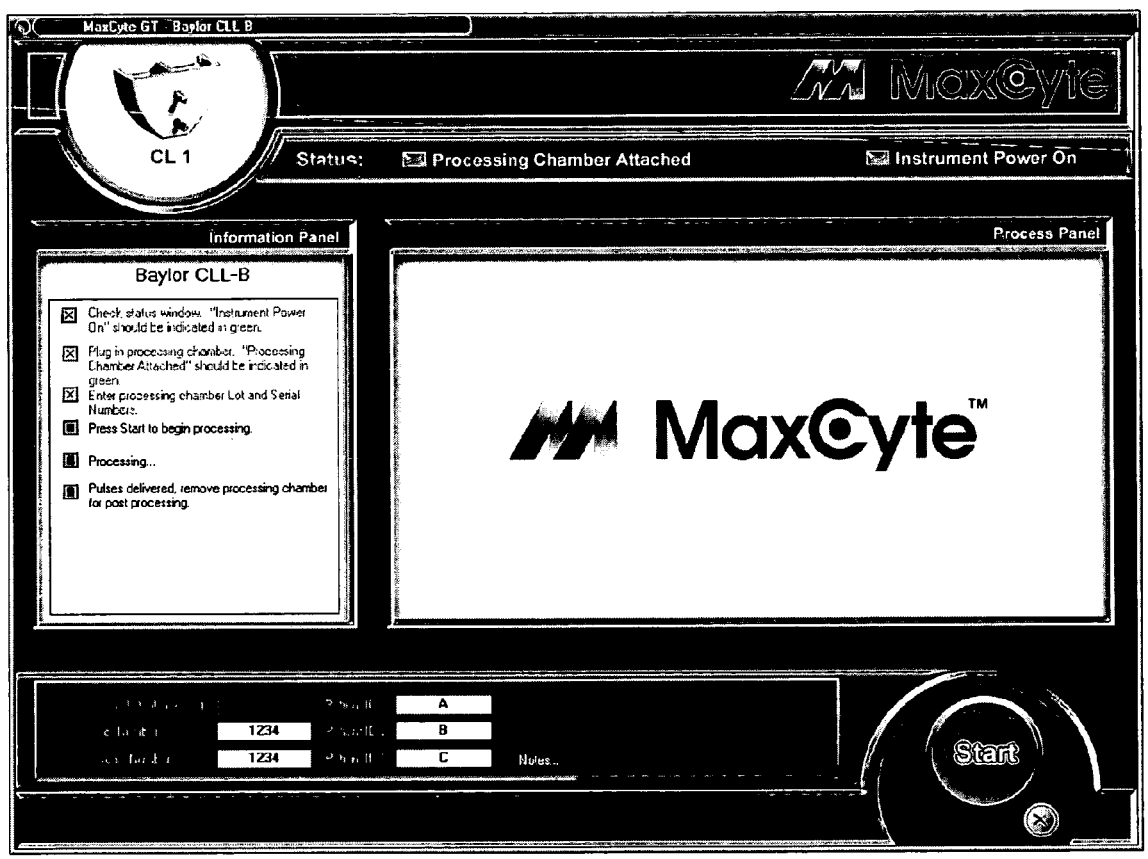
Figure 7:
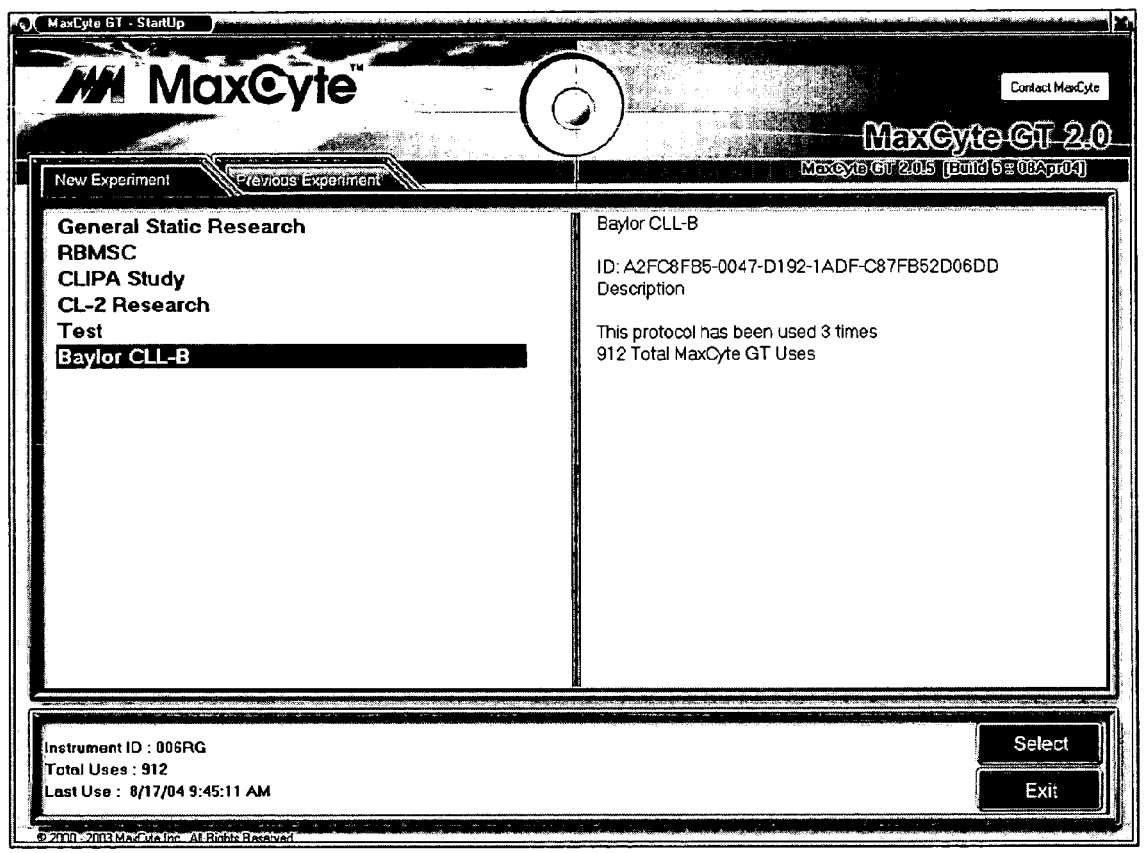

FIGS. 5-7 are example screen shots exhibiting computerized electroporation techniques, and particularly well suited for flow electroporation techniques, in accordance with embodiments of this disclosure.

FIG. 5 is a screen shot of a start up user interface. At the upper left are tabs for "Previous Experiment" and "New Experiment." The Previous Experiment tab is selected in FIG. 5 and shows (in the window at left, under the tab) various experiments that correspond to different processing protocols. In one embodiment, different experiments may, however, be correlated with an identical processing log—for example, two experiments may have different names but may "call" the same underlying processing protocol.

In FIG. 5, the Previous Experiment entitled, "CLIPA Study 040817 0945" is highlighted. To the window at right, the software displays information about that experiment. This window is akin to a processing log display, showing at least some processing information about the experiment. As illustrated, the window shows, from top to bottom, the following fields:

Name of the experiment;
Time (which may be programmed to be time of last run or another pertinent time value);
Instrument ID (identifier for a particular flow electroporation apparatus that ran the experiment);
Use # (indicating what use number the experiment represented for the apparatus);
Protocol Title (indicating the name of the processing protocol);
Protocol ID (indicating an identifier for the processing protocol);
Processing Chamber (indicating a chamber for the experiment);
Patient ID 1-3 (indicating fields to insert patient information);
Processing Chamber Lot and Serial # (indicating lot and serial number associated with the chamber for the experiment);
Process Status (indicating status of the experiment);
Notes (indicating field for miscellaneous use, such as additional patient information and/or notes to a technician).

Below the two main windows in FIG. 5 is an additional window identifying the instrument ID, total uses for that instrument, and the last use date for the instrument. Additionally, the bottom window of FIG. 5 provides two export options to the user for exporting the processing log shown, summarized, associated with, or referenced in the window above. One export option is to export a summary processing log to MS WORD format. The other export option is to e-mail a process log to a party (here, MaxCyte). This export option allows user to e-mail a process log internally or to a third party, which may be useful in allowing internal or third-party review of information for technical support or other reasons. For example, a technician may have a question about a particular aspect of a process, and a processing log may be quickly e-mailed to a support center, which can open the e-mail and talk the technician through any problems.

FIG. 6 is a screen shot of an operating screen for running a processing protocol. In this figure, a processing protocol for the protocol title "Baylor CLL-B" is being executed. At the top of the window is a status display area, which indicates that the processing chamber is attached, and the instrument power is on.

The "information panel" in FIG. 6 provides interactive instructions for the user operating the equipment. As illustrated, step by step instructions corresponding to the processing protocol are displayed. The instructions may be checked-off by the user or checked automatically as the instruction is followed. Shown are the following completed instructions:

Check status to ensure instrument power is on;
Plug in processing chamber and note status confirmation; and
Enter processing chamber Lot and Serial Numbers.

The following three instructions have not yet been completed:

Press start to begin processing;
Processing of sample; and
Remove processing chamber for post-processing.

Of course, additional or different instructions may be provided for any one or more processing protocols. The level of detail in the provided instructions may be dictated by different processing protocols themselves or otherwise. For example, in one embodiment, a first protocol and second protocol may differ only in the amount and/or type of instructions provided to a GUI via programming within the processing protocols themselves or within a software module run by computer 102. One set of instructions for a process may be for more experienced users, while another may be for novice users. In one embodiment, a user may dictate the number and type of instructions to ensure maximum efficiency for any given process.

Sample interactive instructions include, but are not limited to instructions for: checking hardware status of the electroporation apparatus 104, assembling or activating one or more components of the electroporation apparatus 104, handling a sample for introduction into the electroporation apparatus 104, or user input of a data field (e.g., a lot or serial number corresponding to a sample).

FIG. 7 is a screen shot of a start up user interface similar to that of FIG. 5. In FIG. 7, the "New Experiment" tab is selected. It shows (in the window at left, under the tab) various new experiments that correspond to different, new processing protocols. In FIG. 7, the New Experiment entitled, "Baylor CLL-B" is highlighted. To the window at right, the software displays information about that new experiment. This window is akin to a processing log display, showing processing information about the experiment. As illustrated, the window shows, from top to bottom, the following fields:

Name of the experiment;
Process Protocol ID & Description; and
Use information.

Below the two main windows in FIG. 7 is an additional window identifying the instrument ID, total uses for that instrument, and the last use date for the instrument.

FIGS. 8-9 are example process log outputs, in accordance with embodiments of this disclosure. In FIG. 8, a summary processing log is shown. In FIG. 9, a processing log is shown hat includes electrical information as well as information about the processing protocol, patient, and other information. At the bottom of FIG. 9, a processing log can include numeric information regarding sample number, volts, and current. Such information may be plotted, imported into a spreadsheet, or otherwise analyzed according to need. Information such as voltage information may be represented as an average value. The resolution of information within the processing log may vary according to need or desire. In one embodiment, for example, the interval between different voltage values may be about 6 microseconds.

The disclosure and claims should not be limited to the specific preferred or other embodiments described above. For example, even a preferred embodiment is meant simply as an example to help illuminate for the reader one or more techniques being described. With the benefit of the present disclosure, those having ordinary skill in the art will comprehend that techniques claimed here and described above may be modified and applied to a number of additional, different applications, achieving the same or a similar result. The attached claims cover all such modifications that fall within the scope and spirit of this disclosure.

REFERENCES

Each of the following references is hereby incorporated by reference in its entirety:
U.S. patent application Ser. No. 11/127,557
U.S. patent application Ser. No. 10/225,446
U.S. Pat. No. 5,612,207
U.S. Pat. No. 5,720,921
U.S. Pat. No. 6,074,605
U.S. Pat. No. 6,090,617
U.S. Pat. No. 6,485,961
U.S. Pat. No. 6,617,154
U.S. Pat. No. 6,773,669

The invention claimed is:

1. A method comprising:
   (a) controlling an electroporation apparatus with a computer according to one of a plurality of previously-saved, user-defined processing protocols;
   (b) subjecting a sample to electrical energy sufficient to effect electroporation according to the previously-saved, user-defined processing protocol;
   (c) accessing one or more sensors;
   (d) generating a processing log associated with the previously-saved, user-defined processing protocol, the processing log comprising patient information and electrical information, where the electrical information is gathered from the one or more sensors and is associated with the electroporation.

2. The method of claim 1, where the electroporation apparatus comprises a flow electroporation apparatus and where the sample is subjected to the electrical energy while the sample is flowing within the flow electroporation apparatus.

3. The method of claim 1, further comprising:
   (e) exporting the processing log or a summary of the processing log in an encrypted format.

4. The method of claim 1, where the processing log comprises a plurality of fields selected from the group consisting of: file, data, instrument identification, use number, protocol title, protocol description, protocol uses, protocol created, protocol last modified, processing chamber, access level, electroporation equipment information, sample specific information, and patient information.

5. The method of claim 1, further comprising:
   (c) controlling access to the electroporation apparatus according to a security level; and
   (d) generating an audit trail that stores one or more activities of an authorized user.

6. The method of claim 1, further comprising:
   (c) providing interactive instructions to a user, the instructions corresponding to one or more steps of a processing protocol.

7. The method of claim 6, where the interactive instructions comprise instructions for (i) checking hardware status of the flow electroporation apparatus or (ii) assembling or activating one or more components of the flow electroporation apparatus.

8. The method of claim 1, where a previously-saved, user-defined processing protocol corresponds to a processing protocol of a previous experiment.

9. The method of claim 1, further comprising determining if one or materials are validated for use with the electroporation apparatus and prohibiting use if one or more materials are not validated.

10. The method of claim 1, where the electrical information comprises electrical current information.

11. The method of claim 10, where the electrical information comprises successive measurements and the interval between different measurements is less than or equal to about six microseconds.

12. The method of claim 11, where the electrical information comprises a characteristic selected from the group consisting of pulse shape, pattern, polarity, timing, duration, and interval.

13. A method comprising:
   (a) automatically correlating information assigned to a sample with an electroporation processing protocol;
   (b) executing the protocol to electroporate the sample;

(c) accessing one or more sensors;

(d) generating a processing log associated with the electroporation processing protocol, the processing log comprising patient information and electrical information, where the electrical information is gathered from the one or more sensors and is associated with the electroporation.

14. The method of claim 13, where the processing protocol comprises a previously-saved, user-defined processing protocol.

15. The method of claim 13, where the information comprises patient or sample specific information.

16. The method of claim 13, where the information comprises information in a form configured for electronic scanning.

17. The method of claim 16, where the form comprises a bar code.

18. The method of claim 13, where the information comprises a protocol designation corresponding to a previously-saved processing protocol.

19. The method of claim 13, where the information comprises a protocol designation corresponding to a new processing protocol.

20. A method comprising:

(a) scanning a sample to identify information assigned to the sample;

(b) inputting the information;

(c) correlating the information with a pre-existing, electroporation processing protocol;

(d) executing the protocol to electroporate the sample;

(e) accessing one or more sensors; and (f) generating a processing log associated with the pre-existing, electroporation protocol, the processing log comprising patient information and electrical information gathered from the one or more sensors, where the electrical information is associated with the electroporation.

21. The method of claim 20, where scanning comprises use of a radio frequency identification (RFID) tag and reader.

* * * * *